(12) United States Patent
Ishikawa et al.

(10) Patent No.: US 7,507,983 B2
(45) Date of Patent: Mar. 24, 2009

(54) RADIATION IMAGE INFORMATION READING APPARATUS

(75) Inventors: Yoshihiro Ishikawa, Kanagawa-ken (JP); Masakazu Nakajo, Minami-ashigara (JP); Osamu Kuroda, Fujisawa (JP); Yuzuru Ohtsuka, Minami-ashigara (JP); Hideki Suzuki, Kanagawa-ken (JP); Yasunori Ohta, Hadano (JP)

(73) Assignee: FUJIFILM Corporation, Tokyo (JP)

( * ) Notice: Subject to any disclaimer, the term of this patent is extended or adjusted under 35 U.S.C. 154(b) by 225 days.

(21) Appl. No.: 11/225,164

(22) Filed: Sep. 14, 2005

(65) Prior Publication Data

US 2006/0060803 A1    Mar. 23, 2006

(30) Foreign Application Priority Data

Sep. 17, 2004    (JP)    ............... 2004-272464

(51) Int. Cl.
*G01N 23/04* (2006.01)
(52) U.S. Cl. ..................................... 250/584
(58) Field of Classification Search ................ 250/580, 250/581, 582, 583, 584, 585, 586, 587, 588, 250/589, 590, 591
See application file for complete search history.

(56) References Cited

U.S. PATENT DOCUMENTS

| | | | | |
|---|---|---|---|---|
| 5,340,995 A * | 8/1994 | Verbeke et al. | ............... | 250/581 |
| 5,376,806 A * | 12/1994 | Hejazi | ......................... | 250/584 |
| 5,475,230 A * | 12/1995 | Stumpf et al. | ............ | 250/484.4 |
| 6,239,447 B1* | 5/2001 | Toda | ........................... | 250/584 |
| 6,361,040 B1* | 3/2002 | Itakura | ....................... | 271/164 |
| 6,815,703 B2* | 11/2004 | Iwakiri | ....................... | 250/588 |
| 2004/0086164 A1* | 5/2004 | Moriyama et al. | .......... | 382/131 |
| 2004/0169152 A1* | 9/2004 | Tsutoh et al. | ............... | 250/589 |

FOREIGN PATENT DOCUMENTS

JP    2002-156716 A    5/2002

\* cited by examiner

*Primary Examiner*—Christine Sung
(74) *Attorney, Agent, or Firm*—Sughrue Mion, PLLC

(57) ABSTRACT

When cassettes are placed on a conveyor disposed in a cassette loader and detectors disposed on a support plate on the conveyor detect information of identification strips on side walls of the cassettes, the cassettes are judged as being loaded properly in the cassette loader. When the detectors fail to detect the identification strips, the cassettes are judged as not being loaded in a desired state in the cassette loader.

9 Claims, 10 Drawing Sheets

RADIATION IMAGE INFORMATION READING APPARATUS

BACKGROUND OF THE INVENTION

1. Field of the Invention

The present invention relates to an apparatus for reading radiation image information recorded in a stimulable phosphor panel that is stored in a cassette, thereafter erasing remaining radiation image information from the stimulable phosphor panel, and discharging the stimulable phosphor panel.

2. Description of the Related Art

There has heretofore been known a radiation image information reading apparatus employing a stimulable phosphor panel which, when exposed to an applied radiation, stores part of the energy of the radiation, and, when subsequently exposed to applied stimulating rays such as visible light, emits light in proportion to the stored energy of the radiation.

The radiation image information reading apparatus includes a cassette loader for loading a plurality of cassettes each storing a stimulable phosphor panel which records therein radiation image information of a subject such as a human body, a reading unit for applying stimulating light to the stimulable phosphor panel removed from one of the cassettes to read the radiation image information from the stimulable phosphor panel, an erasing unit for applying erasing light to the stimulable phosphor panel from which the radiation image information has been read to erase remaining radiation image information from the stimulable phosphor panel, and a cassette discharger for discharging the stimulable phosphor panel stored in the cassette after the remaining radiation image information has been erased from the stimulable phosphor panel. For details, reference should be made to Japanese Laid-Open Patent Publication No. 2002-156716, for example.

According to Japanese Laid-Open Patent Publication No. 2002-156716, the stimulable phosphor panel is separated from the cassette and supplied to the reading unit. If the cassette is loaded improperly into the cassette loader, the stimulable phosphor panel may not be separated from the cassette. Even if the stimulable phosphor panel is separated from the cassette, the radiation image information cannot properly be read from the stimulable phosphor panel in the event that the stimulable phosphor panel is supplied reversely or upside down to the reading unit.

SUMMARY OF THE INVENTION

It is a general object of the present invention to provide a radiation image information reading apparatus which is capable of determining whether a cassette is properly loaded into a cassette loader or not.

An object of the present invention is to provide a radiation image information reading apparatus which is capable of determining whether a cassette that is loaded into a cassette loader is applicable to the radiation image information reading apparatus or not.

Another object of the present invention is to provide a radiation image information reading apparatus which is capable of adjusting beforehand the loaded state of a cassette in a cassette loader to allow a stimulable phosphor panel stored in the cassette to be processed smoothly.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
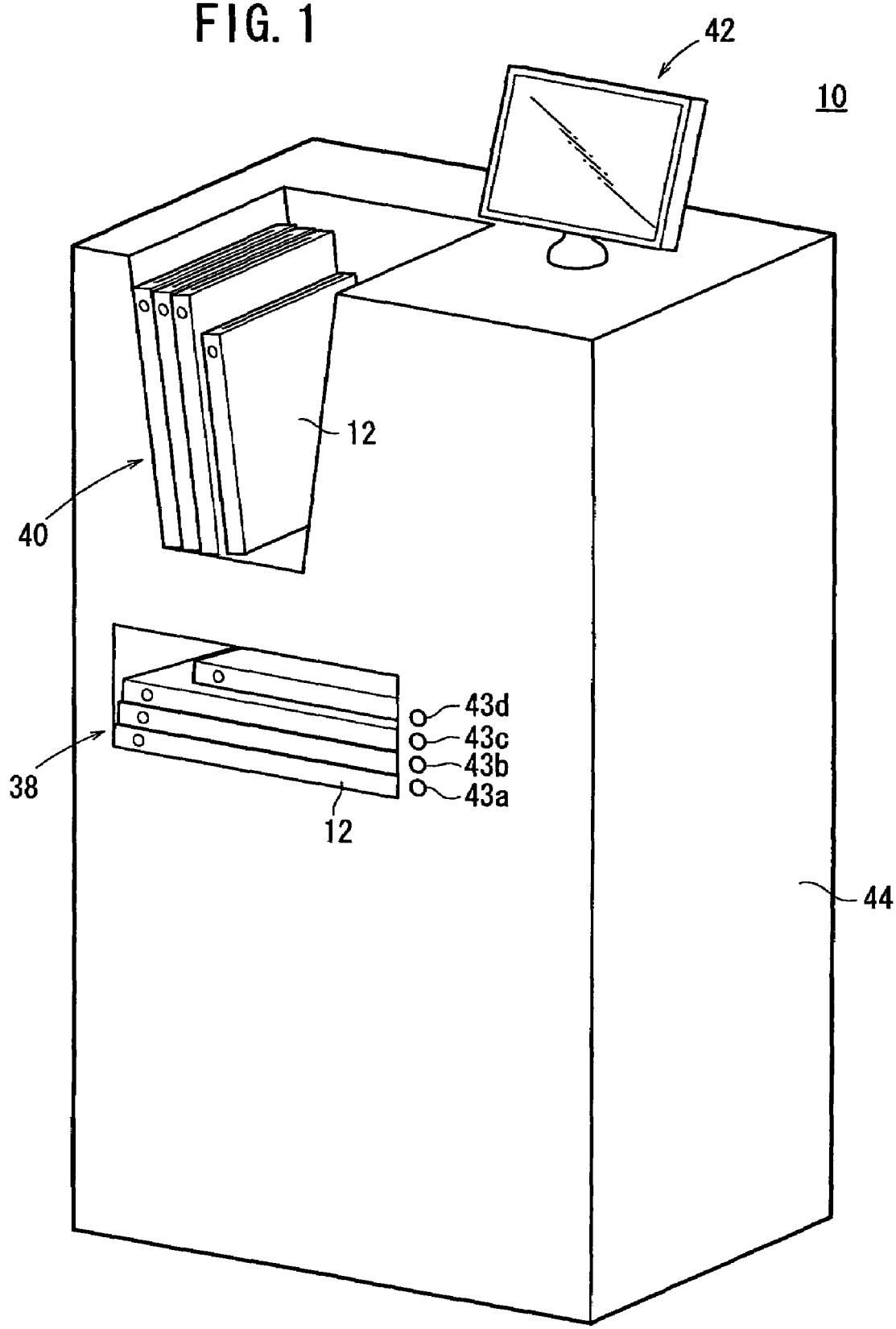
FIG. 1 is a perspective view of a radiation image information reading apparatus according to the present invention.

FIG. 1 shows in perspective a radiation image information reading apparatus 10 according to the present invention.

The radiation image information reading apparatus 10 basically operates as follows. A stimulable phosphor panel 14 (see FIG. 2) is removed from a cassette 12. Radiation image information recorded in the stimulable phosphor panel 14 is read from the stimulable phosphor panel 14, and then remaining radiation image information is erased from the stimulable phosphor panel 14. Thereafter, the stimulable phosphor panel 14 is put back into the cassette 12, which is discharged from the radiation image information reading apparatus 10.

Figure 2:
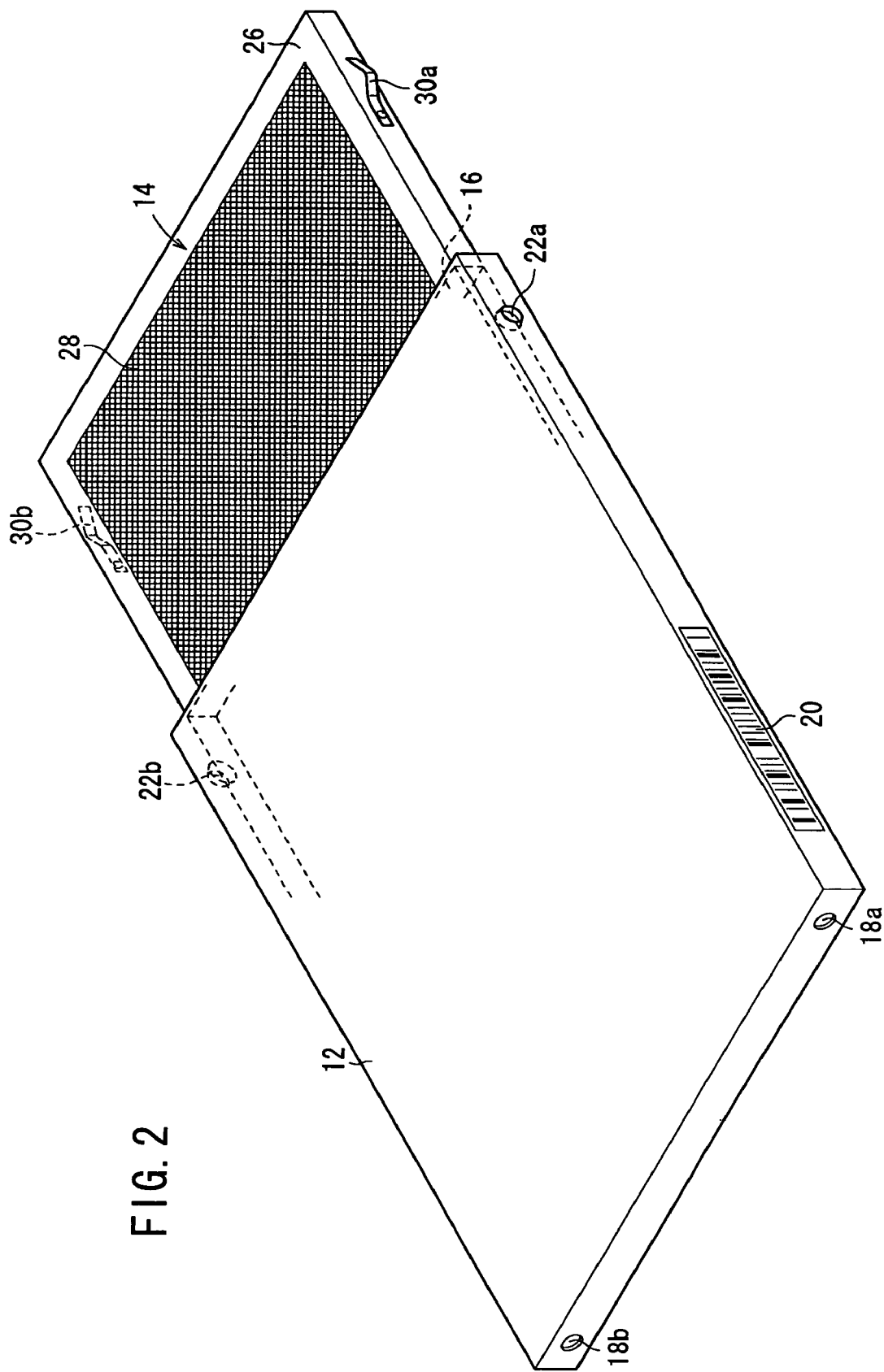
FIG. 2 is a perspective view of a cassette and a stimulable phosphor panel for use in the radiation image information reading apparatus according to the present invention.

As shown in FIG. 2, the cassette 12 has an opening 16 defined in an end thereof for inserting and removing the stimulable phosphor panel 14 therethrough into and out from the cassette 12. The cassette 12 also has insertion holes 18a, 18b defined in an opposite end thereof at spaced locations for inserting ejecting pins (not shown) respectively therethrough to remove the stimulable phosphor panel 14 through the opening 16 from the cassette 12. An identification strip 20 such as a bar-code or the like which represents identification information for specifying the size of the cassette 12 and the stimulable phosphor panel 14 stored in the cassette 12 is applied to one of the side surfaces of the cassette 12. The identification strip 20 also serves to confirm how the cassette 12 is loaded into the radiation image information reading apparatus 10. The cassette 12 also has retaining holes 22a, 22b defined respectively in opposite side walls of the cassette 12 near the opening 16 for retaining the stimulable phosphor panel 14 in the cassette 12.

The stimulable phosphor panel 14 stored in the cassette 12 comprises a hard panel having a columnar stimulable phosphor layer 28 evaporated on a support board 26 which is made of a light-permeable hard material such as glass or the like. The columnar stimulable phosphor layer 28 may be formed by any of various processes including a vacuum evaporation process in which a stimulable phosphor is heated and evaporated in a vacuum container and then deposited on the support board 26, a sputtering process, a CVD process, and an ion plating process. The columnar stimulable phosphor layer 28 has the stimulable phosphor formed as optically independent columns substantially perpendicular to the plane of the stimulable phosphor panel 14. The columnar stimulable phosphor layer 28 is highly sensitive to a radiation applied thereto, lowers the granularity of images recorded therein, and reduces the scattering of stimulating light applied thereto for producing sharp images.

Retainer leaf springs 30a, 30b are mounted respectively on opposite side surfaces of the stimulable phosphor panel 14 near one end thereof. When the stimulable phosphor panel 14 is inserted into the cassette 12, the retainer leaf springs 30a, 30b engage in the respective retaining holes 22a, 22b, thereby securing and retaining the stimulable phosphor panel 14 in the cassette 12. The stimulable phosphor panel 14 can be released from the cassette 12 when unlocking pins (not shown) are inserted respectively into the retaining holes 22a, 22b to push the retainer leaf springs 30a, 30b out of the respective retaining holes 22a, 22b.

The radiation image information reading apparatus 10 has a cassette loader 38 for loading a plurality of cassettes 12 therein, a cassette discharger 40 for discharging a plurality of cassettes 12 that have been processed by the radiation image information reading apparatus 10, and a control display panel 42 for displaying information concerning the processing operation of the radiation image information reading apparatus 10.

The cassette loader 38 is disposed substantially centrally in a front wall of a housing 44 of the radiation image information reading apparatus 10. The cassette loader 38 has a plurality of lamps 43a through 43d (indicators) such as LEDs or the like for indicating loaded states of cassettes 12. The lamps 43a through 43d are disposed on the front wall of the housing 44 laterally of the cassette loader 38. The cassette discharger 40 is disposed as an upwardly open and spread recess in the housing 44 above the cassette loader 38, and is capable of discharging a plurality of erected cassettes 12.

Figure 3:
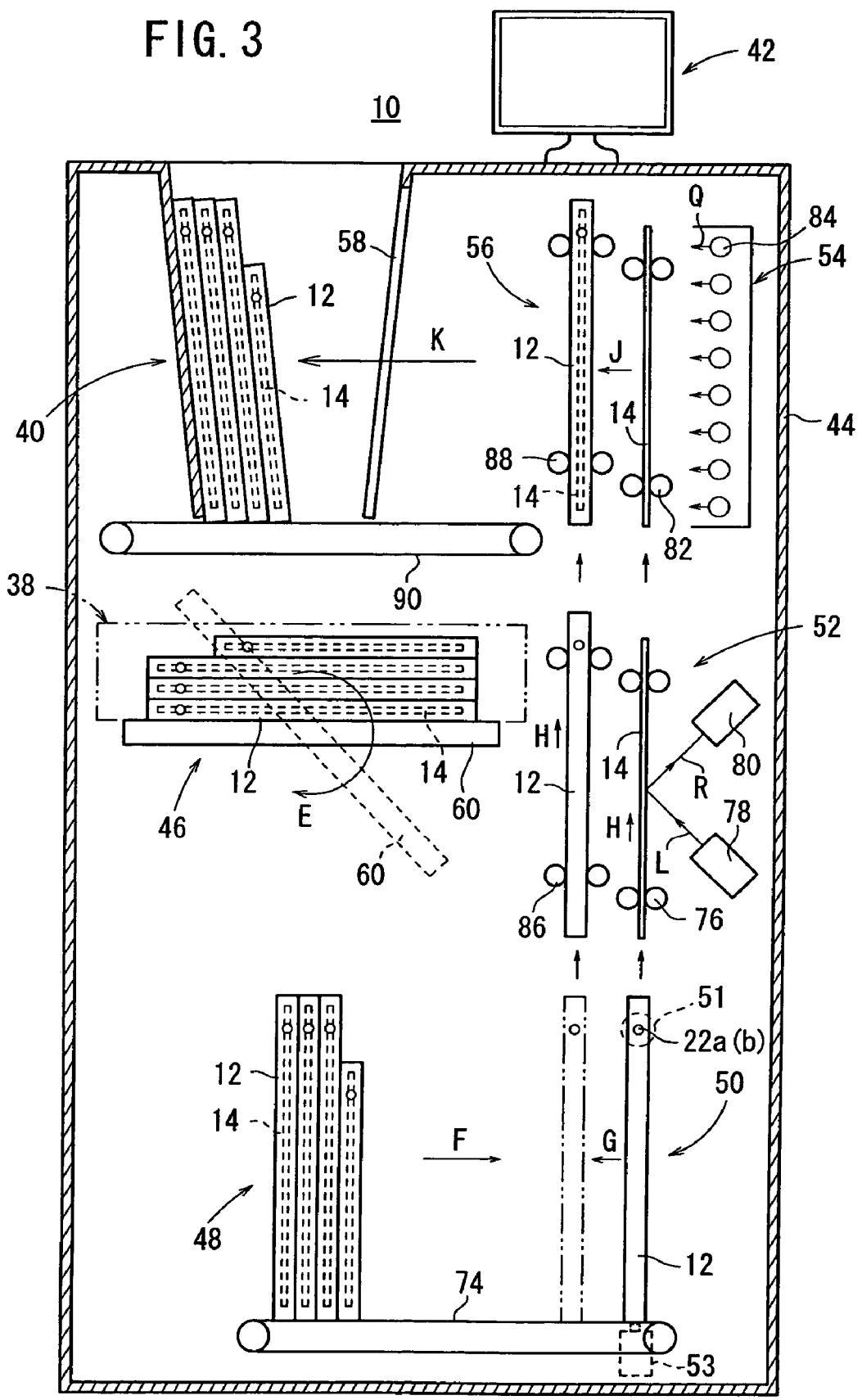
FIG. 3 is a schematic vertical cross-sectional view of the radiation image information reading apparatus according to the present invention.

FIG. 3 shows internal structural details of the radiation image information reading apparatus 10.

As shown in FIG. 3, the radiation image information reading apparatus 10 has, in the housing 44, an attitude changer 46 for changing the attitude of stacked cassettes 12 loaded in the cassette loader 38 into an erected state, a stock unit 48 disposed below the attitude changer 46 for temporarily stocking cassettes 12 which have been erected by the attitude changer 46, a separating unit 50 for separating a stimulable phosphor panel 14 from a cassette 12 that is supplied from the stock unit 48, a reading unit 52 disposed above the separating unit 50 for reading recorded radiation image information from a stimulable phosphor panel 14 that is supplied from the separating unit 50, an erasing unit 54 disposed above the reading unit 52 for erasing remaining radiation image information from a stimulable phosphor panel 14 from which recorded radiation image information has been read, and a storing unit 56 for storing a stimulable phosphor panel 14 supplied from the erasing unit 54 into a cassette 12 that is supplied from the separating unit 50. A cassette 12 in which a stimulable phosphor panel 14 is stored by the storing unit 56 is discharged through a discharge opening 58 into the cassette discharger 40.

Figure 4:
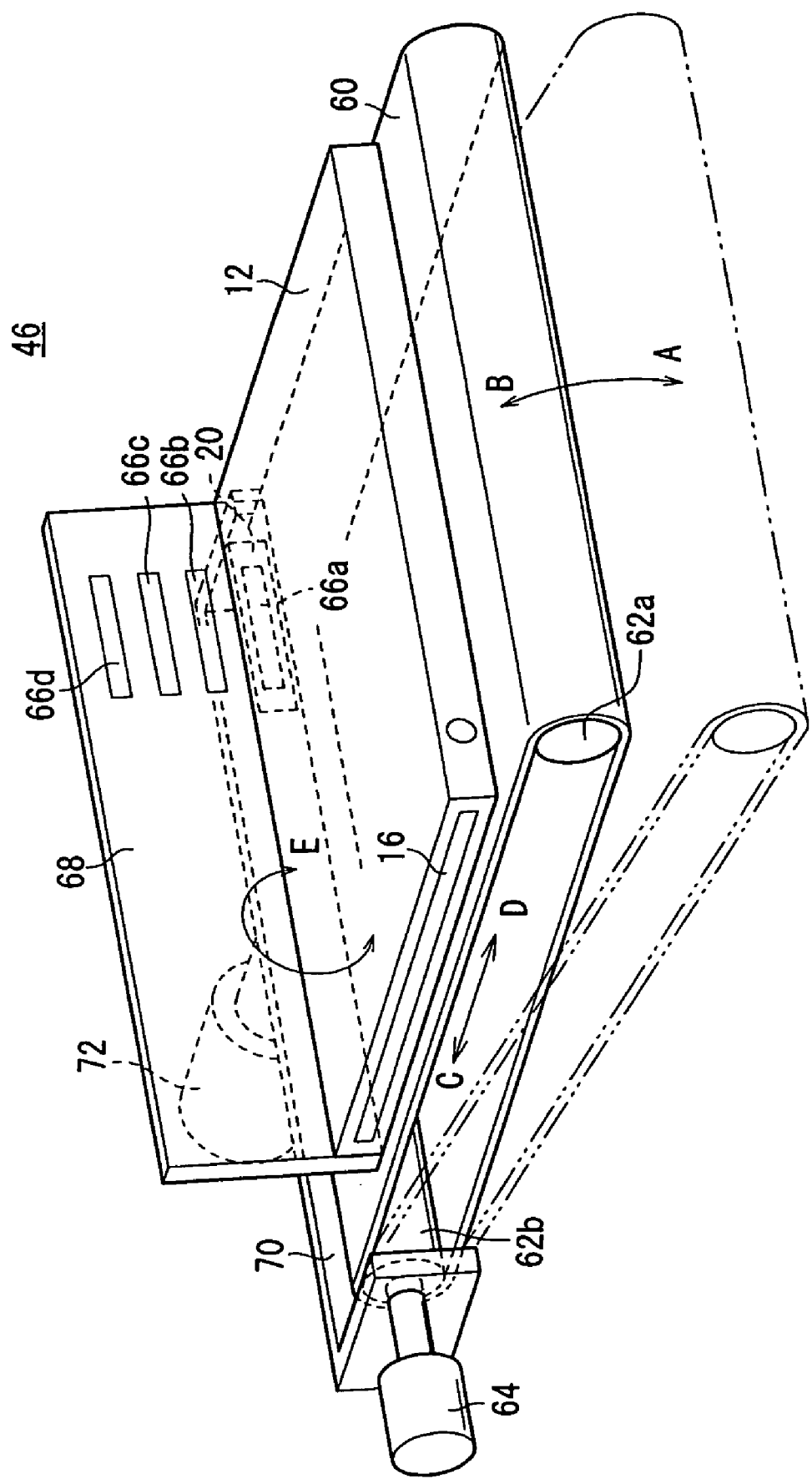
FIG. 4 is a perspective view showing the manner in which a cassette is properly loaded into a cassette loader of the radiation image information reading apparatus according to the present invention.
Figure 5:
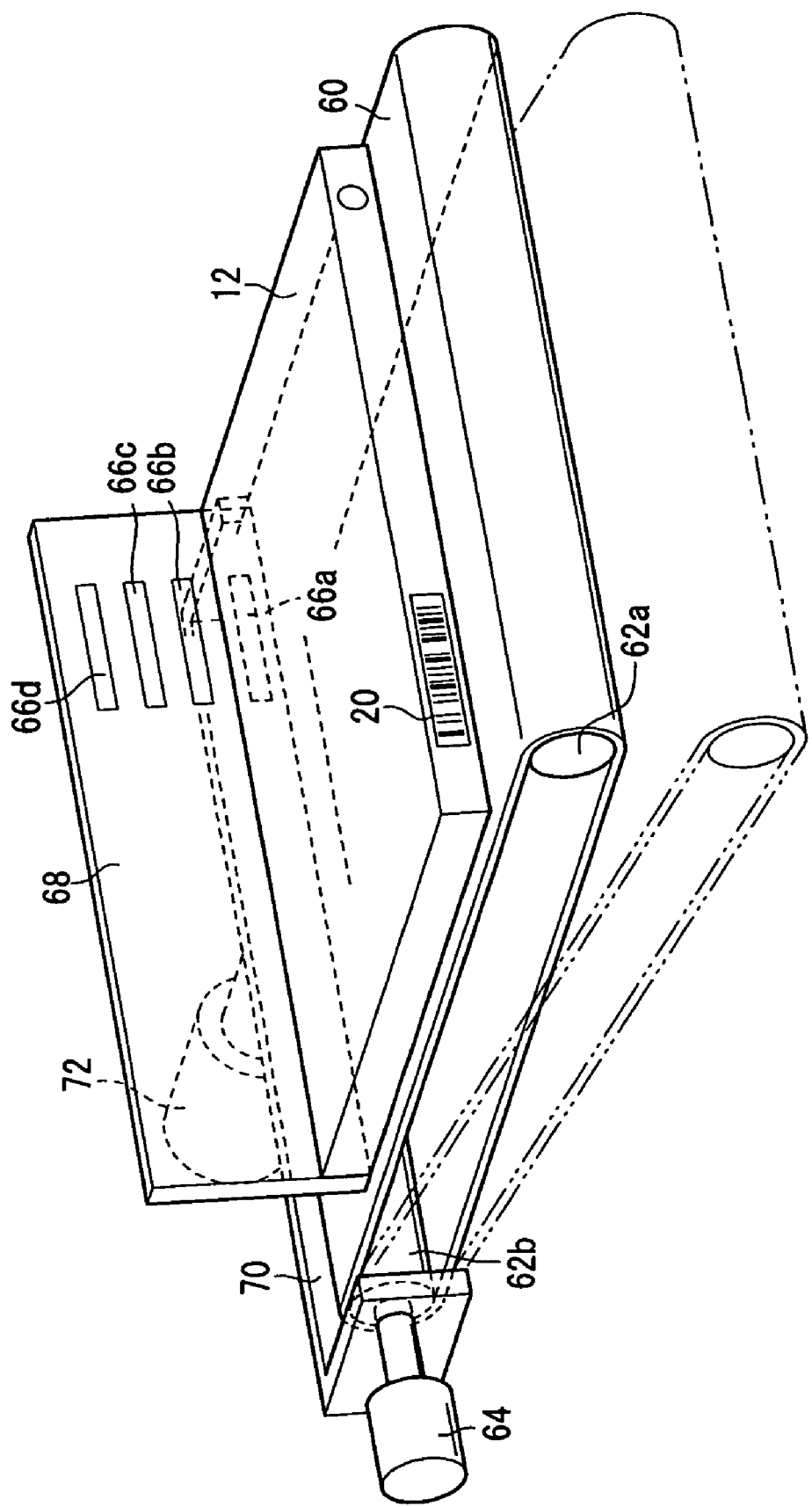
FIG. 5 is a perspective view showing the manner in which a cassette is improperly loaded into the cassette loader of the radiation image information reading apparatus according to the present invention.

As shown in FIGS. 4 and 5, the attitude changer 46 has a conveyor 60 functioning as a support base for supporting cassettes 12 that are loaded into the cassette loader 38. The conveyor 60 is supported by and trained around spaced rotatable shafts 62a, 62b. The rotatable shafts 62a which is positioned closely to the inlet of the cassette loader 38 is vertically displaceable in the directions indicated by the arrows A, B. The rotatable shaft 62b is rotatable by a motor 64 for displacing the conveyor 60 in the directions indicated by the arrows C, D.

On the conveyor 60, there is mounted an upstanding support plate 68 having a plurality of detectors 66a through 66d (detecting means) such as bar-code readers or the like positioned so as to be in alignment with respective identification strips 20 on side walls of stacked cassettes 12 which are placed on the conveyor 60. Alternatively, identification strips 20 may be disposed on ends of cassettes 12 remote from the openings 16 thereof, and the detectors 66a through 66d may be disposed on a side surface of the cassette loader 38 so as to be in alignment with the respective identification strips 20 on the cassettes 12. When the cassettes 12 are placed in the cassette loader 38, the identification strips 20 thereof can accurately be positioned in alignment with the respective detectors 66a through 66d by the support plate 68 which functions as a reference surface.

A motor 72 is connected to the rotatable shaft 62b by a bracket 70. When the motor 72 is energized, the conveyor 60 is rotated selectively in the direction indicated by the arrow E and in the opposite direction of the arrow E. When the conveyor 60 is rotated in the direction indicated by the arrow E, the cassettes 12 stacked on the conveyor 60 are supplied in an erected state to the stock unit 48.

The stock unit 48 and the separating unit 50 are coupled to each other by a horizontally extending conveyor 74. The conveyor 74 serves to supply cassettes 12 stocked in the stock unit 48 in the direction indicated by the arrow F to the separating unit 50, and also to deliver cassettes 12 from the separating unit 50 in the direction indicated by the arrow G. The separating unit 50 has an unlocking mechanism 51 for inserting the unlocking pins into the respective retaining holes 22a, 22b defined in the side walls of the cassette 12 to unlock the stimulable phosphor panel 14 from the cassette 12, and a panel ejecting mechanism 53 for inserting the ejecting pins into the respective insertion holes 18a, 18b defined in the end surface of the cassette 12 to eject the stimulable phosphor panel 14 from the cassette 12.

The reading unit 52 which is disposed above the separating unit 50 has a panel feed mechanism 76 for gripping and feeding the stimulable phosphor panel 14 removed from the cassette 12 in a vertically upward direction, i.e., in the auxiliary scanning direction indicated by the arrow H, a stimulating light scanner 78 for applying stimulating light L in the form of a laser beam to the stimulable phosphor panel 14 fed by the panel feed mechanism 76 while the stimulating light L is being applied in a main scanning direction perpendicular to the auxiliary scanning direction, and a photoelectric transducer 80 such as a photomultiplier, a CCD line sensor, or the like for converting light R which is emitted from the stimulable phosphor panel 14 that is irradiated with the stimulating light L, into an electric signal.

The erasing unit 54 disposed above the reading unit 52 comprises holding rollers 82 for holding a stimulable phosphor panel 14 which is supplied from the reading unit 52, and a plurality of erasing light sources 84 such as halogen lamps, cold-cathode tubes, or the like for applying erasing light Q to the stimulable phosphor panel 14 to erase remaining radiation image information from the stimulable phosphor panel 14. The holding rollers 82 hold the stimulable phosphor panel 14 and moves the stimulable phosphor panel 14 in the direction indicated by the arrow J to supply the stimulable phosphor panel 14 to the storing unit 56.

Between the reading unit 52 and the attitude changer 46, there is disposed a cassette feed mechanism 86 for feeding vertically upwardly an empty cassette 12 from which a stimulable phosphor panel 14 has been removed. The cassette 12 fed by the cassette feed mechanism 86 is supplied to the storing unit 56 where a stimulable phosphor panel 14 is waiting.

The storing unit 56 has holding rollers 88 for holding a cassette 12. The holding rollers 88 supply a cassette 12 in which a stimulable phosphor panel 14 is stored to a conveyor 90. The conveyor 90, which extends horizontally, connects the storing unit 56 and the cassette discharger 40, and feeds the cassette 12 in the direction indicated by the arrow K from the storing unit 56 to the cassette discharger 40.

The radiation image information reading apparatus 10 is basically constructed as described above. Operation of the radiation image information reading apparatus 10 will be described below.

The operator loads a cassette 12 storing therein a stimulable phosphor panel 14 with radiation image information recorded therein into the cassette loader 38. The cassette loader 38 is capable of storing a plurality of stacked cassettes 12 having different sizes. Therefore, the operator can easily load a plurality of cassettes 12 simultaneously into the cassette loader 38. It is assumed in the present embodiment that the cassette loader 38 is capable of loading a maximum of four cassettes 12 at the same time.

When the cassettes 12 are placed on the conveyor 60 of the attitude changer 46 in the cassette loader 38, the detectors 66a through 66d on the support plate 68 detect how the respective cassettes 12 are loaded.

Specifically, if the cassettes 12 are loaded properly into the cassette loader 38 as shown in FIG. 4, then since the identification strips 20 on the side surfaces of the cassettes 12 are aligned with and face the respective detectors 66a through 66d, the detectors 66a through 66d correctly read the information of the identification strips 20, judging that the cassettes 12 are properly loaded. The properly loaded states of the cassettes 12 as judged by the detectors 66a through 66d are indicated to the operator, for example, by turning on the lamps 43a through 43d at the cassette loader 38 according to a predetermined pattern. The detectors 66a through 66d also acquire the information of the cassettes 12 from the identification strips 20 in addition to determining how the cassettes 12 are loaded.

If the cassettes 12 are loaded improperly into the cassette loader 38 as shown in FIG. 5, or if cassettes of another modality are loaded into the radiation image information reading apparatus 10, then since the detectors 66a through 66d cannot read the information of the identification strips 20, the detectors 66a through 66d judge that the cassettes 12 are improperly loaded. The improperly loaded states of the cassettes 12 as judged by the detectors 66a through 66d are indicated to the operator by turning on the lamps 43a through 43d according to another predetermined pattern. Having confirmed how the lamps 43a through 43d are turned on, the operator can correct the loaded states of the cassettes 12.

The loaded states of the cassettes 12 may be detected otherwise. For example, reflective markers disposed on certain areas of the cassettes 12 may be optically detected by reflected light. Alternatively, electrode terminals disposed on certain areas of the cassettes 12 may be electrically detected by electric contact with electrode terminals on the support plate 68. Further alternatively, shapes or certain patterns of sides of the cassettes 12 may be imaged by an image capturing device such as a CCD camera or the like, and loaded states of the cassettes 12 may be detected by analyzing the captured images.

Figure 6:
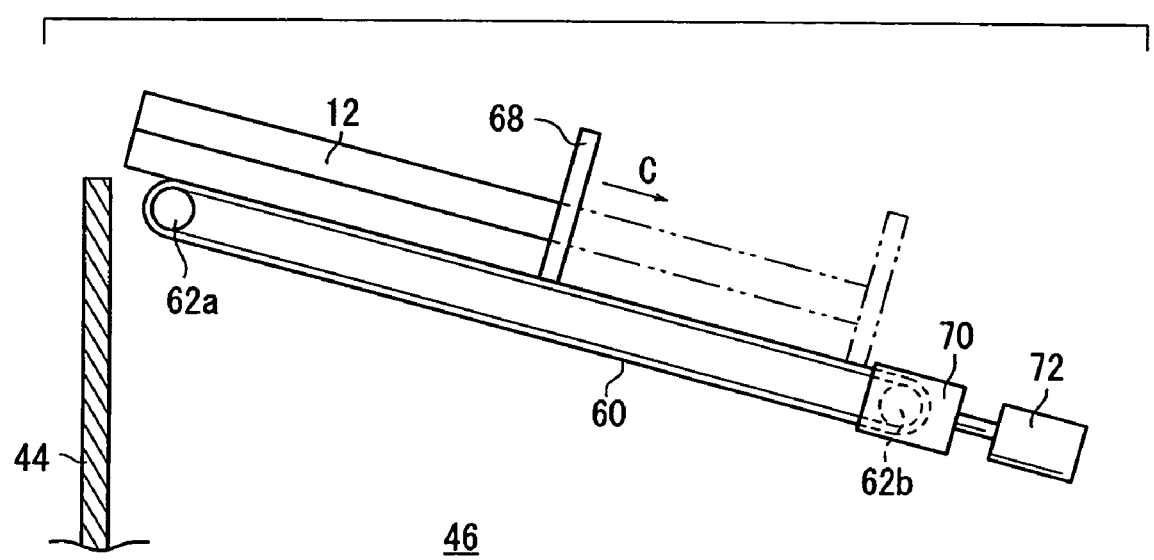
FIG. 6 is a schematic side elevational view showing the manner in which an attitude changer of the radiation image information reading apparatus according to the present invention operates.
Figure 7:
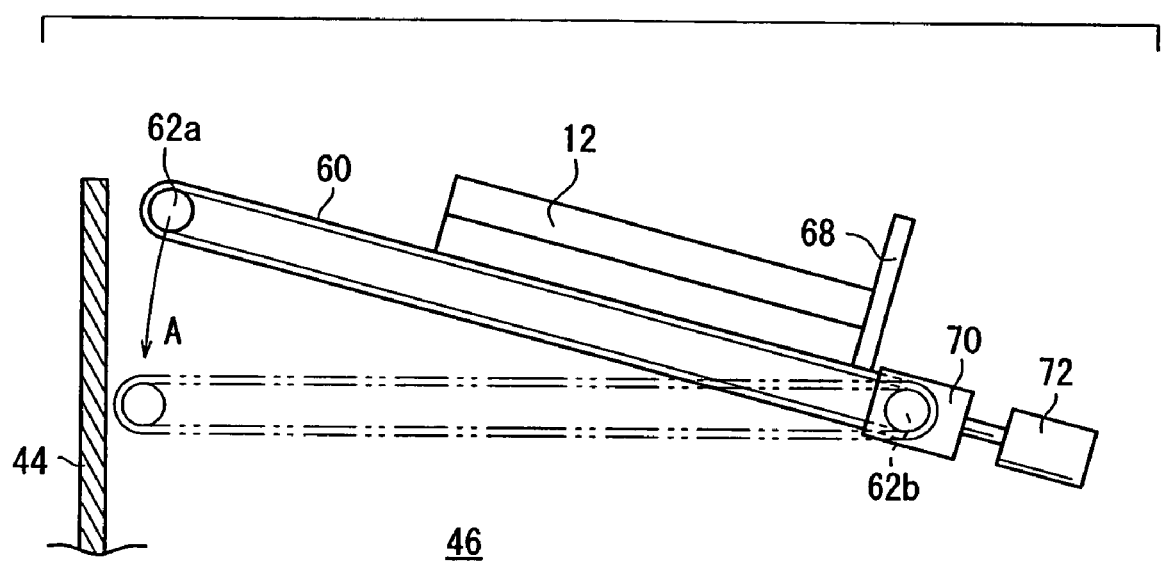
FIG. 7 is a schematic side elevational view showing the manner in which the attitude changer of the radiation image information reading apparatus according to the present invention operates.

When it is confirmed that the cassettes 12 are properly loaded into the cassette loader 38, the motor 64 is energized to displace the conveyor 60 of the attitude changer 46 together with the support plate 68 in the direction indicated by the arrow C, bringing the cassettes 12 into the radiation image information reading apparatus 10 (see FIG. 6). Then, the conveyor 60 is rotated about the rotatable shaft 62b in the direction indicated by the arrow A by an actuator (not shown), and brought into a horizontal attitude (see FIG. 7).

Figure 8:
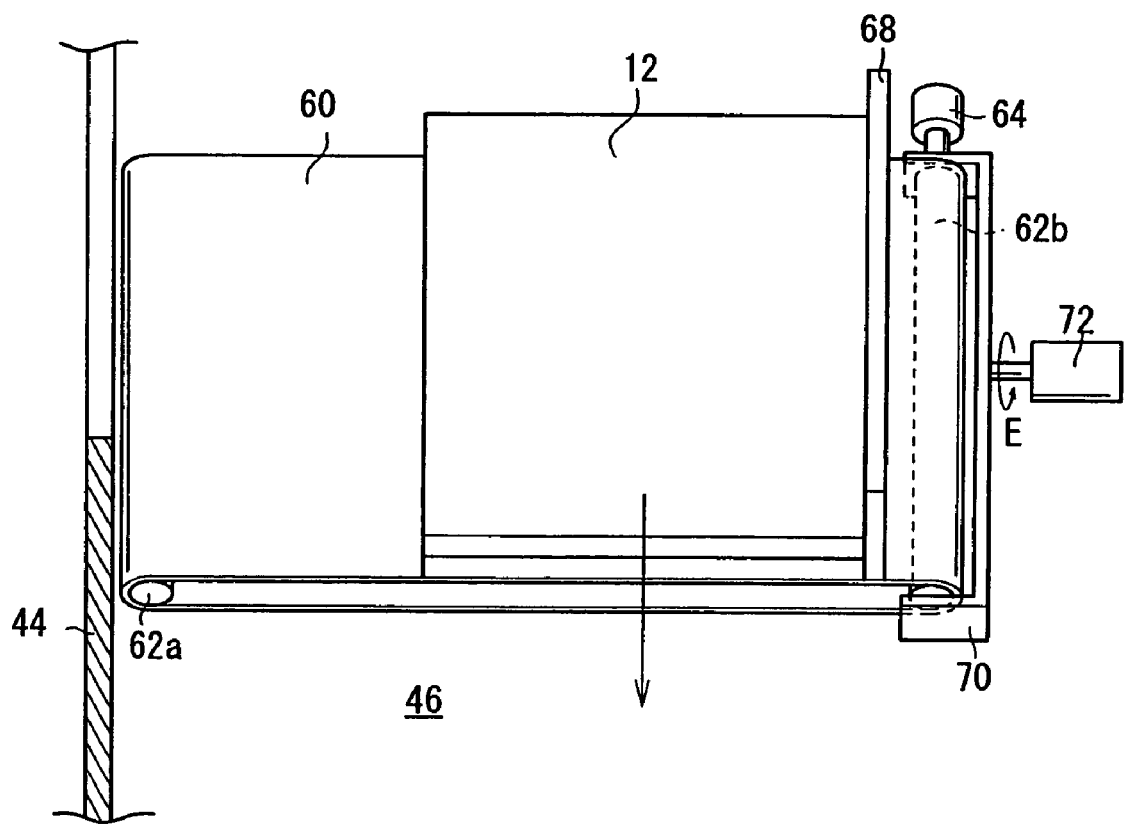
FIG. 8 is a schematic perspective view showing the manner in which the attitude changer of the radiation image information reading apparatus according to the present invention operates.

After the conveyor 60 is brought into the horizontal attitude, the motor 72 is energized to cause the bracket 70 to turn the conveyor 60 in the direction indicated by the arrow E (see FIG. 8). The cassettes 12 stacked on the conveyor 60 are now transferred from the attitude changer 46 to the stock unit 48, and stocked in an erected state in the stock unit 48 on the conveyor 74 (see FIG. 3).

After having transferred the cassettes 12 to the stock unit 48, the conveyor 60 of the attitude changer 46 is rotated in the opposite direction of the arrow E (see FIG. 4) back to the horizontal position, after which the rotatable shaft 62a is lifted in the direction indicated by the arrow B for receiving a next batch of cassettes 12 to be loaded into the cassette loader 38. Therefore, different batches of cassettes 12 can be placed respectively in the cassette loader 38 and the stock unit 48.

The cassettes 12 stocked in the stock unit 48 are then fed in the direction indicated by the arrow F by the conveyor 74, and supplied to the separating unit 50. In the separating unit 50, the unlocking pins of the unlocking mechanism 51 are inserted respectively into the retaining holes 22a, 22b of the cassette 12, pushing the retainer leaf springs 30a, 30b to release the stimulable phosphor panel 14 from the cassette 12. Then, the ejecting pins of the panel ejecting mechanism 53 are inserted respectively into the insertion holes 18a, 18b of the cassette 12, ejecting the stimulable phosphor panel 14 out of the cassette 12 and supplying the stimulable phosphor panel 14 to the reading unit 52 above the separating unit 50.

In the reading unit 52, the stimulable phosphor panel 14 is gripped by the panel feed mechanism 76 and fed thereby in the vertically upward direction, i.e., in the auxiliary scanning direction indicated by the arrow H. While the stimulable phosphor panel 14 is being fed in the auxiliary scanning direction, it is irradiated with the stimulating light L which is emitted from the stimulating light scanner 78 and applied in the main scanning direction. The stimulable phosphor panel 14 emits light R representative of the recorded radiation image information upon exposure to the stimulating light L. The emitted light R is converted by the photoelectric transducer 80 into an electric signal representative of the recorded radiation image information.

The stimulable phosphor panel 14 from which the recorded radiation image information has been read is then supplied to the erasing unit 54 that is disposed above the reading unit 52.

In the erasing unit 54, the erasing light Q emitted from the erasing light sources 84 is applied to the stimulable phosphor panel 14, erasing remaining radiation image information from the stimulable phosphor panel 14.

Since the reading unit 52 reads the recorded radiation image information from the stimulable phosphor panel 14 while the stimulable phosphor panel 14 is being fed in the vertically upward direction and the erasing unit 54 erases the remaining radiation image information from the stimulable phosphor panel 14 while the stimulable phosphor panel 14 is being fed in the vertically upward direction, the radiation image information reading apparatus 10 takes up a minimum floor space and hence has a reduced size regardless of the size of the cassettes 12 that are used.

After the remaining radiation image information has been erased from the stimulable phosphor panel 14 by the erasing unit 54, the stimulable phosphor panel 14 is held by the holding rollers 82 and supplied in the direction indicated by the arrow J to the storing unit 56.

The cassette 12 from which the stimulable phosphor panel 14 has been removed by the separating unit 50 is displaced a certain distance in the direction indicated by the arrow G, and then supplied to the cassette feed mechanism 86 by which the cassette 12 is fed vertically upwardly in the direction indicated by the arrow H. Then, the cassette 12 is supplied to the storing unit 56 where the stimulable phosphor panel 14 waiting in the storing unit 56 is placed back into the cassette 12.

The cassette 12 with the stimulable phosphor panel 14 stored therein is supplied to the conveyor 90 by the holding rollers 88. Then, the conveyor 90 feeds the cassette 12 in the direction indicated by the arrow K into the cassette discharger 40.

The cassette discharger 40 holds a plurality of cassettes 12 in an erected state. Therefore, the cassette discharger 40 can stock a number of cassettes 12 therein. Since the cassettes 12 are not vertically stacked in the cassette discharger 40, the operator can easily pick up a desired one of the cassettes 12 from the cassette discharger 40 for recording a next image in the stimulable phosphor panel 14 in the cassette 12. Because the cassette discharger 40 is spread upwardly towards the opening thereof, the operator can select a desired one of the cassettes 12 by manually sorting the cassettes 12 laterally.

The reading process in the reading unit 52, the erasing process in the erasing unit 54, and the feeding process in the cassette feed mechanism 86, in which empty cassettes 12 are fed, can be performed concurrently with each other. Therefore, the radiation image information reading apparatus 10 can process a plurality of cassettes 12 highly efficiently.

Figure 9:
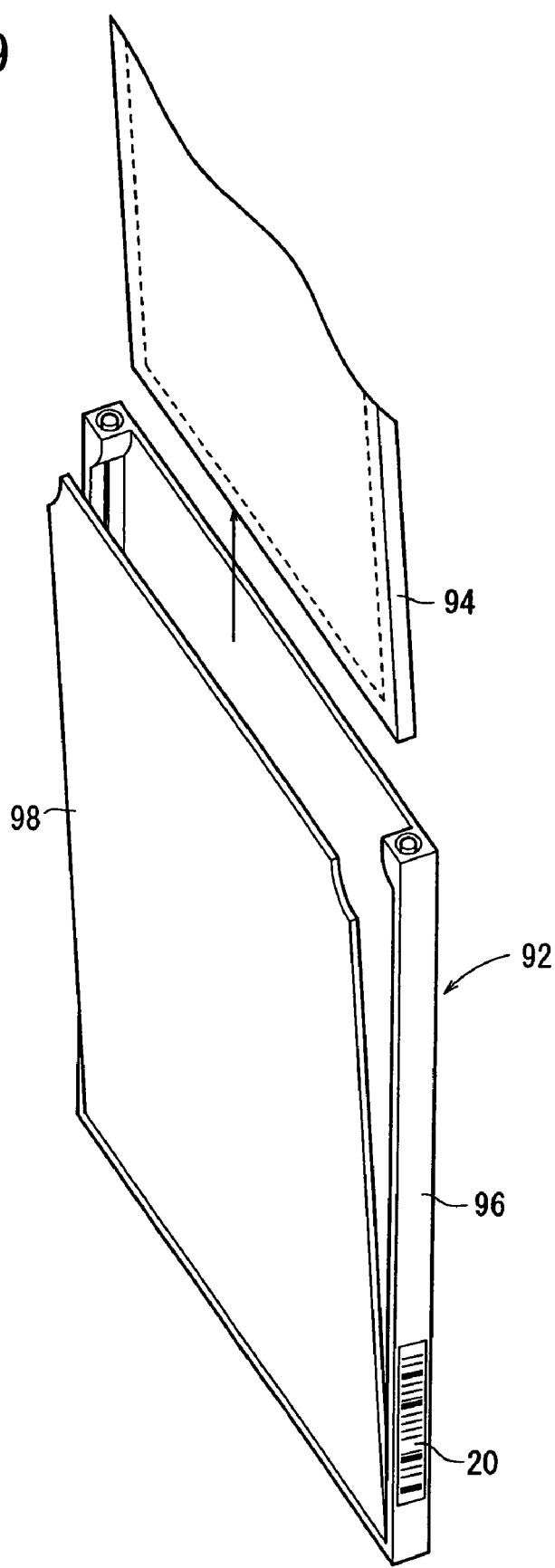
FIG. 9 is a perspective view of another cassette and another stimulable phosphor panel which can be used in the radiation image information reading apparatus according to the present invention.

In the above embodiment, the radiation image information reading apparatus 10 uses the cassette 12 and the stimulable phosphor panel 14 shown in FIG. 2. However, the radiation image information reading apparatus 10 may use a cassette 92 and a stimulable phosphor panel 94 as shown in FIG. 9. As shown in FIG. 9, the cassette 92 has a casing 96 and a lid 98 pivoted to the casing 96, and the stimulable phosphor panel 94 is placed between the casing 96 and the lid 98.

The radiation image information reading apparatus 10 which uses the cassette 92 and the stimulable phosphor panel 94 operates as follows. After the cassette 92 is delivered from the stock unit 48 to the separating unit 50, the lid 98 is opened by a lid opening mechanism (not shown), and the stimulable phosphor panel 94 is removed from the cassette 92 and supplied to the reading unit 52 for reading recorded radiation image information and then to the erasing unit 54 for erasing remaining radiation image information. The cassette 92, from which the stimulable phosphor panel 94 has been removed, is fed by the cassette feed mechanism 86 to the storing unit 56, where the lid 98 is opened again and the stimulable phosphor panel 94 is stored back into the cassette 92. The cassette 92 is then delivered to the cassette discharger 40.

Figure 10:
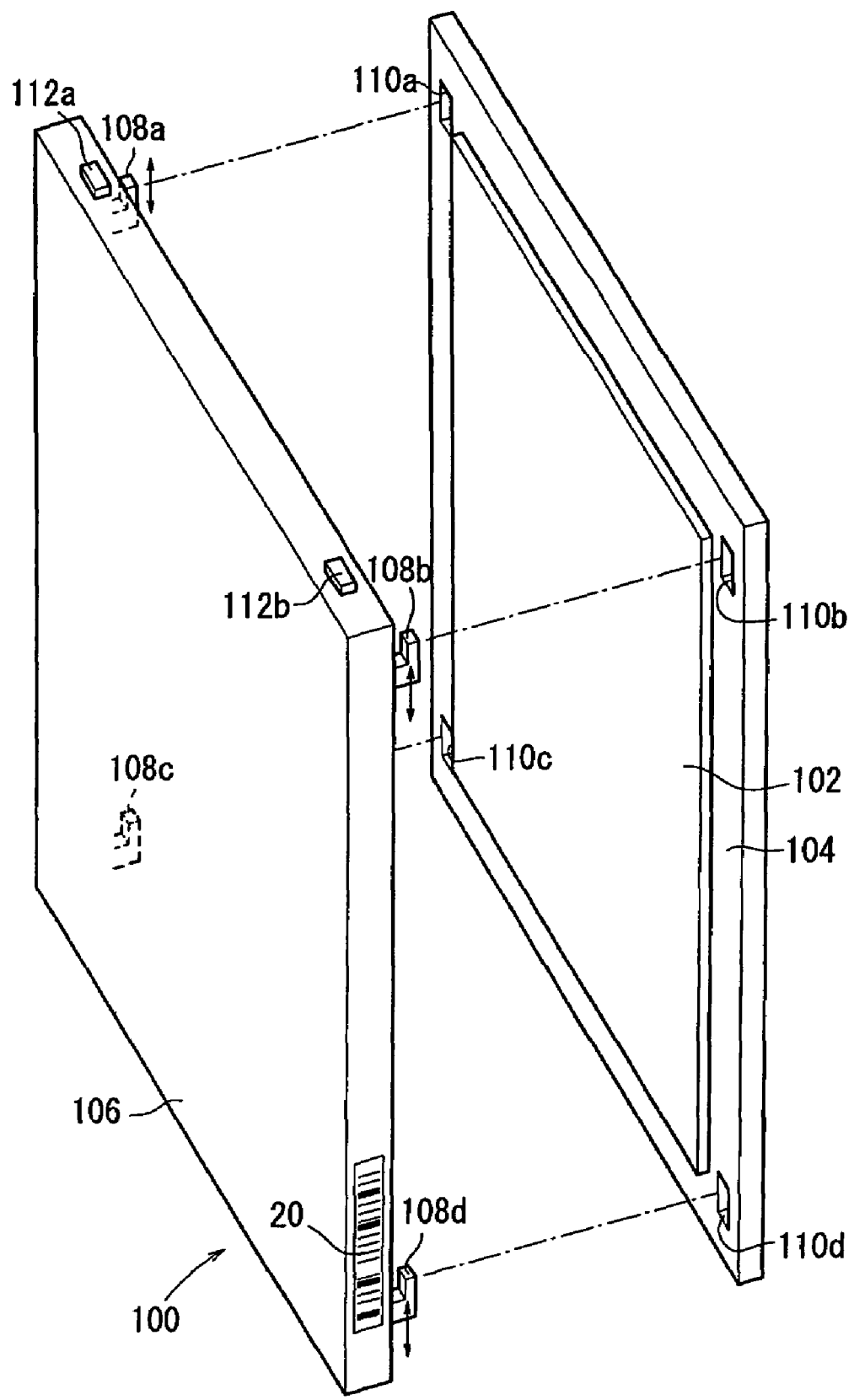
FIG. 10 is an exploded perspective view of still another cassette and still another stimulable phosphor panel which can be used in the radiation image information reading apparatus according to the present invention.

FIG. 10 shows a cassette 100 and a stimulable phosphor panel 102 which can also be used in the radiation image information reading apparatus 10. As shown in FIG. 10, the cassette 100 has a support base 104 for supporting the stimulable phosphor panel 102 thereon and a lid 106 for protecting the stimulable phosphor panel 102. The lid 106 is removably coupled to the support base 104 by a plurality of fingers 108a through 108d engaging in respective slots 110a through 110d defined in the support base 104. The fingers 108a through 108d are movable with respect to the lid 106 in the directions indicated by the arrows, and are coupled to push buttons 112a, 112b disposed on an end face of the lid 106.

The radiation image information reading apparatus 10 which uses the cassette 100 and the stimulable phosphor panel 102 operates as follows. After the cassette 100 is delivered from the stock unit 48 to the separating unit 50, the push buttons 112a, 112b are pushed by a lid opening mechanism (not shown) to release the fingers 108a through 108d from the slots 110a through 110d. The lid 106 is now detached from the support base 104, and the stimulable phosphor panel 102 is supplied together with the support base 104 to the reading unit 52 for reading recorded radiation image information and then to the erasing unit 54 for erasing remaining radiation image information. The reading unit 52 and the erasing unit 54 should preferably be arranged such that the reading process and the erasing process are performed from the side of the stimulable phosphor panel 102 supported on the support base 104. The lid 106, from which the stimulable phosphor panel 102 has been removed, is fed by the cassette feed mechanism 86 to the storing unit 56, where the lid 106 is combined with the support base 104 holding the stimulable phosphor panel 102 from which the remaining radiation image information has been erased. Thereafter, the cassette 100 is delivered to the cassette discharger 40.

Although certain preferred embodiments of the present invention have been shown and described in detail, it should be understood that various changes and modifications may be made therein without departing from the scope of the appended claims.

What is claimed is:

1. An apparatus for reading radiation image information, comprising:

a cassette loader for loading a cassette storing therein a stimulable phosphor panel with radiation image information recorded therein;

a reading unit for applying stimulating light to said stimulable phosphor panel which is removed from said cassette supplied from said cassette loader to emit light from said stimulable phosphor panel, and photoelectrically reading the light emitted from said stimulable phosphor panel to obtain the radiation image information recorded in said stimulable phosphor panel;

an erasing unit for applying erasing light to said stimulable phosphor panel to erase remaining radiation image information therefrom;

a cassette discharger for discharging said cassette storing said stimulable phosphor panel therein;

said cassette loader having detecting means disposed in alignment with a particular area of said cassette which is loaded in a certain state, for detecting information of said particular area, whereby the loaded state of said cassette in said cassette loader is determined based on the information detected by said detecting means, wherein said detecting means comprises an image capturing means for capturing image information representing a shape or a pattern of said particular area, and wherein said image capturing means performs imaging by a charge-coupled device to produce an image signal to determine an orientation of the cassette.

2. An apparatus according to claim 1, wherein said cassette loader has an indicator for indicating a detected state of the information detected by said detecting means.

3. An apparatus according to claim 2, wherein said indicator comprises an LED for indicating the loaded state of said cassette.

4. An apparatus according to claim 1, wherein the information of said particular area includes size information of said cassette.

5. An apparatus according to claim 1, wherein the information of said particular area includes management information of said stimulable phosphor panel stored in said cassette.

6. An apparatus according to claim 1, wherein said cassette loader comprises a support base which is inclinable for supporting said cassette, and a support plate disposed on a lower end of said inclined support base for supporting a side surface of said cassette, said detecting means being mounted on said support base.

7. An apparatus according to claim 1, wherein said cassette loader is arranged to support a plurality of said cassettes in a stacked state, said cassette loader having a plurality of said detecting means for detecting information of said particular areas of said cassettes, respectively, in the stacked state.

8. An apparatus according to claim 1, wherein an attitude of a support base is inclinable from a loading state to an erected state, wherein the cassette is erected to a vertical position.

9. An apparatus for reading radiation image information, comprising:

a cassette loader for loading a cassette storing therein a stimulable phosphor panel with radiation image information recorded therein;

a reading unit for applying stimulating light to said stimulable phosphor panel which is removed from said cassette supplied from said cassette loader to emit light from said stimulable phosphor panel, and photoelectrically reading the light emitted from said stimulable phosphor panel to obtain the radiation image information recorded in said stimulable phosphor panel;

an erasing unit for applying erasing light to said stimulable phosphor panel to erase remaining radiation image information therefrom;

a cassette discharger for discharging said cassette storing said stimulable phosphor panel therein;

said cassette loader having detecting means disposed in alignment with a particular area of said cassette which is loaded in a certain state, for detecting information of said particular area, whereby the loaded state of said cassette in said cassette loader is determined based on the information detected by said detecting means, wherein said detecting means detects information by contacting an electrode terminal disposed in said particular area, and wherein an attitude of a support base is inclinable from a loading state to an erected state, wherein the cassette is erected to a vertical position.

* * * * *